United States Patent
Daunes-Marion et al.

(10) Patent No.: US 11,045,510 B2
(45) Date of Patent: Jun. 29, 2021

(54) COMBINATION OF AQUEOUS EXTRACTS OF WATERCRESS AND NASTURTIUM AND ATP FOR USE IN THE TREATMENT OF ALOPECIA

(71) Applicant: PIERRE FABRE DERMO-COSMETIQUE, Boulogne-Billancourt (FR)

(72) Inventors: Sylvie Daunes-Marion, Toulouse (FR); Marguerite Lévêque, Toulouse (FR); Stéphane Poigny, Saubens (FR)

(73) Assignee: PIERRE FABRE DERMO-COSMETIQUE, Boulogne-Billancourt (FR)

( * ) Notice: Subject to any disclaimer, the term of this patent is extended or adjusted under 35 U.S.C. 154(b) by 24 days.

(21) Appl. No.: 16/494,612

(22) PCT Filed: Mar. 16, 2018

(86) PCT No.: PCT/EP2018/056655
§ 371 (c)(1),
(2) Date: Sep. 16, 2019

(87) PCT Pub. No.: WO2018/167265
PCT Pub. Date: Sep. 20, 2018

(65) Prior Publication Data
US 2020/0085896 A1    Mar. 19, 2020

(30) Foreign Application Priority Data

Mar. 17, 2017    (FR) ...................................... 1752231

(51) Int. Cl.
*A61K 8/9789*    (2017.01)
*A61K 36/31*    (2006.01)
*A61K 8/49*    (2006.01)
*A61K 8/97*    (2017.01)
*A61Q 5/00*    (2006.01)
*A61Q 7/00*    (2006.01)

(52) U.S. Cl.
CPC ............ *A61K 36/31* (2013.01); *A61K 8/4926* (2013.01); *A61K 8/97* (2013.01); *A61Q 5/00* (2013.01); *A61Q 7/00* (2013.01)

(58) Field of Classification Search
CPC .................................................... A61K 8/9789
See application file for complete search history.

(56) References Cited

FOREIGN PATENT DOCUMENTS

| CN | 1939479 A | 4/2007 |
|---|---|---|
| EP | 0035919 A2 | 9/1981 |
| FR | 2821271 A1 | 8/2002 |

OTHER PUBLICATIONS

English language bibliographic information for Suzuki, JP 01-042416 A, 1989.*
Mintel, "GNPD-Nasturtium & Lemon Shampoo," Nov. 1, 2006, pp. 1-2, XP055394195.
Mintel, "LT High Performance Hair Stimulating Shampoo." Jan. 31, 2014, pp. 1-9, XP-002770577.
SOLABIA, "Cressatine® Hair Booster, " Jan. 1, 2016, 1 page, XP055394202.

* cited by examiner

*Primary Examiner* — Rosanne Kosson
(74) *Attorney, Agent, or Firm* — Birch, Stewart, Kolasch & Birch, LLP

(57) ABSTRACT

The present invention relates to a novel combination comprising an extract of watercress, an extract of Indian cress, and ATP, and to the use of said combination in the field of hair science, more particularly in the treatment or prevention of alopecia.

14 Claims, No Drawings

COMBINATION OF AQUEOUS EXTRACTS OF WATERCRESS AND NASTURTIUM AND ATP FOR USE IN THE TREATMENT OF ALOPECIA

The present invention relates to a novel combination of an aqueous extract of watercress and an extract of Indian cress in combination with ATP, and to the use of said combination in the field of hair science, more particularly in the treatment or prevention of alopecia.

The hair follicle is a mini-organ anchored in the skin to the hypodermis, whose principal function is the production of a hair shaft. Their distribution is established during growth in utero and their number is genetically determined. The hair follicle is a dynamic structure which produces the hair during cycles of growth and of tissue remodelling. This cycle can be broken down into 3 phases:

A growth phase (anagen): the dermal papilla cells (fibroblasts) send a signal to the bulb stem cells which allows their proliferation. These cells transform and envelope the dermal papilla to form the sulphur matrix of the hair. They divide and differentiate into keratinocytes, cells responsible for the structure of the hair. The length of this phase determines the length of the hair and depends on the proliferation and differentiation of the matrix cells at the base of the follicle.

A regression phase (catagen): the matrix dies and consequently the dermal papilla loses contact with said matrix. Exchange between the cells stops. The follicle and the dermal papilla rise towards the epidermis.

A rest phase (telogen): the cells of the dermal papilla and of the bulb are intact and inactive. The hair falls out. For a new hair to develop, the cycle must be reinitiated.

The development and growth of the hair follicle are influenced by compounds expressed by the dermal papilla: proteins such as Wnt and growth factors such as keratinocyte growth factor (KGF) and epithelium growth factor (EGF).

The head of hair is thus continually renewed; out of the 100,000 to 150,000 hairs which make up a head of hair, the majority is in growth phase.

The term "alopecia" refers to the partial or general loss of hair. Many factors can be involved in alopecia, such as, for example, genetic factors, age, sex, diseases, stress, hormonal problems, the side effects of drugs. Several forms of alopecia can be distinguished:

Androgenetic alopecia: this is the most common alopecia. Early hair loss occurs in genetically predisposed individuals and affects mostly men. It is manifested by a decrease in the volume of hair, possibly baldness, and affects 50% of men over 50 years of age;

Postmenopausal alopecia: this is the most common cause of baldness in women. In women, hair loss is more diffuse and extensive than in men. Female diffuse alopecia is a disorder which often begins at menopause and which concerns about 40% of women over 70. The term "diffuse" indicates that, in contrast to men, hair loss effects the entire scalp in a uniform manner;

Acute alopecia: it can be linked to chemotherapeutic treatment, stress, significant nutritional deficiencies, iron deficiency, hormonal disorders;

Scarring alopecia: it can be caused by skin problems (tumours, burns, alopecia areata), acute irradiation, lupus erythematosus or parasites (ringworm, lichen);

Alopecia areata: it seems to be autoimmune and characterized by bald spots of varying sizes and location;

Congenital alopecia: rare, it corresponds to a lack of roots or to hair abnormalities (mutations).

Alopecia is essentially linked to a disruption in hair renewal which leads, at first, to an increase of the frequency of cycles at the expense of hair quality and then hair quantity. The most common phenomenon is a reduction of the growth cycle (anagen phase) due to a halt in cell proliferation. This results in a premature induction of the catagen phase, a greater number of hair follicles in the telogen phase, and consequently to a greater hair loss. To fight hair loss, it is thus necessary to revive the hair cycle, for example, by activating the anagen phase.

To fight this hair loss, several processes have been used. Some aim to increase blood flow by irradiation or massage, other methods make use of external treatment or treatment by local injections of products containing stimulatory, tonic and bactericidal chemical substances such as salicylic acid, resorcin, alcohols, sulphamides, acetylcholine, choline, betaine, pantothenic acid, etc. Other processes endeavour to influence cellular exchange using vitamin F or B-complex, hormones of various origins, cholesterin, lecithin, or products of keratin. Sulphur and mercury or thallium salts have been proposed for their disinfectant and curative action. Lastly, cortisone and adrenocorticotropic hormone (ACTH) are known by the fact that they slow hair loss and produce hair regeneration, but only during their administration, which is done for other reasons and their action on the hair disappears after a few weeks, when the treatment is discontinued. In recent years, the use of adenosine triphosphate (ATP) was disclosed in anti-hair-loss treatment, as energy source for the follicular papilla in order to prolong the life of the hair. In the cell, ATP is the principal energy source, the precursor of cofactors $NAD^+$ and coenzyme A. Moreover, ATP is an intermediate in cell communication. It plays an essential role in numerous tissues by its action on $P_2Y$ and $P_2X$ purinergic receptors. In the human hair follicle, expression of $P_2Y$ and $P_2X$ receptors has been shown in distinct compartments during the anagen phase, suggesting a role of ATP in the physiology of the hair follicle.

Surprisingly, the inventors discovered that the combination of ATP with an extract of watercress, in particular an aqueous extract of watercress, in particular an aqueous extract of watercress leaves, and an extract of Indian cress, in particular an aqueous extract of Indian cress, induced a synergistic action on hepatocyte growth factor (HGF) and on keratinocyte growth factor (KGF), detailed in Example 1.

As a product which is particularly well suited to the invention, mention may be made of the commercial material Cressatine® sold by the company Solabia. Cressatine® is an active agent obtained by aqueous extraction of the aerial parts of watercress (*Nasturtium officinale*) and of Indian cress (*Tropaeolum majus*), stabilized with plant glycerine; this active agent contains an equivalent amount of watercress and of Indian cress. This active agent was designed to facilitate hair growth and to strengthen hair from the roots. It participates in the initiation of hair regeneration via the Wnt pathway. Finally, it extends the length of the growth phase by means of the Wnt pathway.

In a first embodiment, the invention relates to a combination comprising an extract of watercress, more particularly an aqueous extract of watercress, even more particularly an aqueous extract of watercress aerial parts, and still even more particularly an aqueous extract of leaves of watercress; an extract of Indian cress, particularly an aqueous extract of Indian cress, even more particularly an aqueous extract of Indian cress aerial parts, and ATP.

ATP, or adenosine 5'-triphosphate, is a nucleotide of the purine family serving to store and transport energy (purines are nitrogenous bases). It consists of adenine (a nitrogenous base), ribose (a sugar with five carbon atoms) and three phosphate groups linked together by two pyrophosphate bonds having high potential energy. ATP is highly soluble in water. It remains relatively stable in aqueous solution at pH values between 6.8 and 7.4.

Within the context of the invention, ATP can be used optionally in salt form, optionally in hydrated form.

Preferentially, an ATP salt will be used, such as a salt with Na, Ca, Mg, for example, optionally hydrated.

A monosodium or disodium salt, monohydrate or dihydrate, can thus be used in particular.

In particular, the ATP can be adenosine 5'-triphosphate disodium hydrate.

In a second embodiment, the invention relates to a combination according to embodiment 1, for use in the prevention and/or treatment of alopecia.

In a third embodiment, the invention relates to a combination for use according to embodiment 1, wherein the alopecia is selected from the group consisting of androgenetic alopecia, postmenopausal alopecia, acute alopecia and alopecia areata.

In a fourth embodiment, the invention relates to a cosmetic use of the combination according to embodiment 1, to promote hair growth.

In a fifth embodiment, the invention relates to a cosmetic or dermatological composition comprising as anti-alopecia active principle a combination according to embodiment 1, with at least one cosmetically or dermatologically acceptable excipient.

In a sixth embodiment, the invention relates to a composition according to embodiment 5, characterized in that it comprises 0.01 to 0.5 wt % of an extract of watercress, more particularly an aqueous extract of watercress, relative to the total weight of the composition.

In a seventh embodiment, the present invention relates to a composition according to one of embodiments 5 or 6, characterized in that it comprises 0.01 to 0.5 wt % of an extract of Indian cress, more particularly an aqueous extract of Indian cress, relative to the total weight of the composition.

In an eighth embodiment, the invention relates to a composition according to one of embodiments 5 to 7, characterized in that it comprises 0.1 to 0.5 wt % of ATP relative to the total weight of the composition.

In a ninth embodiment, the invention relates to a composition according to any one of embodiments 5 to 8, characterized in that it further comprises another anti-alopecia active principle.

In a tenth embodiment, the invention relates to a composition according to any one of embodiments 5 to 9, characterized in that it comes in a form suitable for topical application.

In an eleventh embodiment, the invention relates to a cosmetic use of a cosmetic composition according to any one of embodiments 5 to 10 to promote hair growth.

In a twelfth embodiment, the invention relates to a dermatological composition according to one of embodiments 5 to 10, for use in the prevention and/or treatment of alopecia.

In a thirteenth embodiment, the invention further relates to a process for cosmetic care of the hair intended to improve the aesthetic quality of the hair by promoting hair growth, characterized in that it consists in applying to the hair and the scalp an effective amount of a combination comprising an extract of watercress, more particularly an aqueous extract of watercress; an extract of Indian cress, more particularly an aqueous extract of Indian cress, and ATP according to the first embodiment or of a cosmetic composition according to one of embodiments 5 to 10, in leaving same in contact with the hair, and optionally in rinsing the hair. More particularly the aqueous extract of watercress is an aqueous extract of watercress aerial parts, and even more particularly an aqueous extract of watercress leaves. Particularly, the extract of Indian cress is an aqueous extract of Indian cress aerial parts, in particular of leaves.

The expression "improve the aesthetic quality of the hair" means in particular that the head of hair provides greater coverage and/or that the scalp is less visible.

The present invention thus relates to a combination of an extract of watercress, more particularly an aqueous extract of watercress, and an extract of Indian cress, more particularly an aqueous extract of Indian cress, in combination with ATP.

The aqueous extract of watercress is preferentially an extract of watercress leaves. Watercress, or *Nasturtium officinale*, is a member of the family Brassicaceae. Watercress is a perennial plant which forms creeping shoots at the bottom of the body of water, then hollow stems which rise out of water at the end of the branches. The stems are spread out, perhaps lying over the ground or over stretches of water. They can exceed two meters in length. Watercress has a record level of iron and calcium as well as a lot of vitamin C. Sewn in a nursery in compost kept moist or in the open, watercress can develop, be bedded out and be harvested about three months after sowing and a month after bedding out.

The extract of watercress used according to the invention is an aqueous extract of watercress, preferentially an aqueous extract of watercress aerial parts, more particularly an aqueous extract of watercress stems and/or leaves. Even more particularly, an extract suitable for the invention is well-known to the person skilled in the art and listed under CAS No. 84775-70-2; it is composed of aqueous extract of watercress leaves and stems.

The aqueous extract of Indian cress is preferentially an aqueous extract of Indian cress aerial parts, more particularly of Indian cress leaves.

Indian cress (*Tropaeolum majus*) is an annual or perennial herbaceous plant of the family Tropaeolaceae and the genus *Tropaeolum*. This ornamental plant is edible. Indian cress is rich in vitamin C, especially its foliage; furthermore, it is often harvested without the flowers from May to October. The juice of the plant when fresh has antiseptic, stimulatory, expectorant and diuretic properties. The plant contains a glucosinolate (glucotropaeolin) and an enzyme, myrosinase, which hydrolyses the former to thiocyanates, isothiocyanates and nitriles, molecules having toxic activity against herbivorous insects.

The seeds, the leaves and the flowers are used, fresh or dried, in herbal medicine.

The extract of Indian cress used according to the invention is an aqueous extract of Indian cress, preferentially an aqueous extract of Indian cress aerial parts, more particularly an aqueous extract of Indian cress flowers, stems and/or leaves. Even more particularly, an extract of Indian cress suitable for the invention is well-known to the person skilled in the art and listed under CAS No. 84625-49-0; it is composed of aqueous extract of Indian cress aerial parts, in particular an extract of Indian cress flowers, leaves and/or stems, more particularly of leaves.

A product combining both extracts, of Indian cress and of watercress, particularly preferred for preparing the combination according to the invention is Cressatine®, marketed by the company Solabia®. As indicated above, such a product is available commercially and corresponds to a mixture of an aqueous extract of watercress (*Nasturtium officinale*) leaves and of an aqueous extract of Indian cress (*Tropaeolum majus*) leaves, stabilized with plant glycerine and titrated with sulphur (200 mg/kg).

In a particular embodiment the combination according to the invention is a combination consisting of an aqueous extract of watercress, an aqueous extract of Indian cress and ATP.

Preferentially, the present invention relates to the use of the combination of an extract of watercress, particularly an aqueous extract of watercress, and an extract of Indian cress, more particularly an aqueous extract of Indian cress, in combination with ATP in the prevention and/or treatment of alopecia. More particularly the aqueous extract of watercress is an aqueous extract of watercress aerial parts, and even more particularly an aqueous extract of watercress leaves. Particularly, the extract of Indian cress is an aqueous extract of Indian cress aerial parts, in particular of leaves.

More particularly, the present invention relates to the use of the combination of extracts of watercress and of Indian cress, more particularly of aqueous extracts of watercress and of Indian cress, preferentially stabilized with plant glycerine, and ATP for the prevention and/or treatment of androgenetic alopecia, postmenopausal alopecia, acute alopecia or alopecia areata. Advantageously, the present invention relates to the use of the combination of an extract of watercress, preferentially an aqueous extract of watercress and an extract of Indian cress, preferentially an aqueous extract of Indian cress, in combination with ATP for the prevention and/or treatment of androgenetic alopecia. More particularly the aqueous extract of watercress is an aqueous extract of watercress aerial parts, and even more particularly an aqueous extract of watercress leaves. Particularly, the extract of Indian cress is an aqueous extract of Indian cress aerial parts, in particular of leaves.

The present invention also relates to the use of the combination of an extract of watercress, particularly an aqueous extract of watercress, and an extract of Indian cress, particularly an aqueous extract of Indian cress, in combination with ATP to promote hair growth. More particularly the aqueous extract of watercress is an aqueous extract of watercress aerial parts, and even more particularly an aqueous extract of watercress leaves. Particularly, the extract of Indian cress is an aqueous extract of Indian cress aerial parts, in particular of leaves.

The invention also relates to the use of the combination of an extract of watercress, particularly an aqueous extract of watercress, and an extract of Indian cress, particularly an aqueous extract of Indian cress, in combination with ATP for use in the prevention and/or treatment of alopecia, in a form suitable for administration via the topical route and/or via the oral route. More particularly the aqueous extract of watercress is an aqueous extract of watercress aerial parts, and even more particularly an aqueous extract of watercress leaves. Particularly, the extract of Indian cress is an aqueous extract of Indian cress aerial parts, in particular of leaves.

In another aspect, the present invention relates to the cosmetic or dermatological use of the combination of an extract of watercress, particularly an aqueous extract of watercress, and an extract of Indian cress, particularly an aqueous extract of Indian cress, in combination with ATP to limit the loss of head/body hair and/or to promote the growth thereof and/or to increase the density of hair follicles. More particularly the aqueous extract of watercress is an aqueous extract of watercress aerial parts, and even more particularly an aqueous extract of watercress leaves. Particularly, the extract of Indian cress is an aqueous extract of Indian cress aerial parts, in particular of leaves.

In another aspect, the present invention also relates to a cosmetic or dermatological process for limiting the loss of head/body hair and/or promoting the growth thereof and/or increasing the density of hair follicles comprising a step of administering to an individual the combination of an extract of watercress, particularly an aqueous extract of watercress, and an extract of Indian cress, particularly an aqueous extract of Indian cress, in combination with ATP. More particularly the aqueous extract of watercress is an aqueous extract of watercress aerial parts, and even more particularly an aqueous extract of watercress leaves. Particularly, the extract of Indian cress is an aqueous extract of Indian cress aerial parts, in particular of leaves.

The present invention can be used in combination with known treatments for alopecia or with molecules known to promote the growth of head/body hair or to limit the loss thereof such as for example finasteride, minoxidil or to benefit an individual who has undergone or is to undergo a micrograft.

The present invention can also be used in combination with compounds useful for good hair structure, such as for example sulphur-containing proteins, vitamin B6 and various minerals such as zinc and/or magnesium.

The term "head/body hair" means head hair, body hair, eyebrows, lashes and/or coat. Preferentially, "head/body hair" refers to head hair.

The term "alopecia" means total or partial hair loss for example linked to reduced hair growth and/or to accelerated head/body hair loss. This term includes but is not limited to androgenetic alopecia, postmenopausal alopecia, acute alopecia, scarring alopecia, alopecia areata, congenital alopecia. The consequences of alopecia are a temporary or permanent, partial or total absence of hair.

The term "to treat alopecia" means to stop alopecia, to reduce alopecia and/or to mitigate alopecia. Thus "to treat alopecia" includes limiting hair loss, promoting hair growth, increasing hair follicle density and/or regulating the phases of the hair follicle cycle.

The term "to prevent" means to decrease the risk of developing alopecia, or to slow the progression of alopecia in a mammal, preferentially men who are likely to develop alopecia.

The term "to limit" means to slow, to reduce, to diminish and or stop.

The term "to promote" means to increase, to enhance, to help, to amplify and/or to accelerate.

The present invention also relates to a cosmetic or dermatological composition for preventing and or treating alopecia comprising a combination comprising an extract of watercress and of Indian cress, particularly an aqueous extract of watercress and of Indian cress, preferentially stabilized with plant glycerine, and ATP with a cosmetically or dermatologically acceptable excipient, particularly acceptable for topical application and/or for an oral route. More particularly the aqueous extract of watercress is an aqueous extract of watercress aerial parts, and even more particularly an aqueous extract of watercress leaves. Particularly, the extract of Indian cress is an aqueous extract of Indian cress aerial parts, in particular of leaves.

Another object of the present invention relates to a dermatological composition for use in the treatment of alopecia, and especially androgenetic alopecia, comprising as active principle the combination according to the invention. In a particular embodiment, the combination according to the invention is the sole anti-alopecia active principle of the composition.

In the present invention, the expression "cosmetically or dermatologically acceptable" refers to that which is useful in the preparation of a cosmetic or dermatological composition, which is generally safe, nontoxic and neither biologically nor otherwise undesirable and which is acceptable for cosmetic use, especially by topical application and/or via the oral route.

The cosmetic or dermatological compositions according to the invention can come in the forms which are usually known for topical administration, i.e., notably lotions, shampoos, balms, foams, gels, dispersions, emulsions, sprays, serums, masks or creams, with excipients in particular allowing penetration in order to improve the properties and the accessibility of the active principles.

Advantageously the compositions according to the invention can come in the forms which are usually known for topical administration on the hair and the scalp, i.e., notably a shampoo, a conditioner, a hair cream, a hair lotion or a no-rinse spray.

Formulated products which can be rinsed are thus distinguished from those which are not.

The invention thus relates to cosmetic or dermatological compositions according to one of the embodiments of the present invention, characterized in that they come in a form suitable for and adapted to topical application.

Advantageously a cosmetological and/or dermatological topical composition according to the invention is characterized in that it comes in the form of three distinct phases, intended to be mixed immediately before use so as to obtain an emulsion and/or a microemulsion, said phases being a solid phase in a powdery form, an aqueous phase and a lipophilic phase.

In such a configuration, the components of the combination according to the invention, the extract of watercress, in particular the aqueous extract of watercress, the extract of Indian cress, in particular the aqueous extract of Indian cress, and ATP are comprised in physically separate compartments. In particular, the aqueous extract of watercress and the aqueous extract of Indian cress can be present in the same compartment of the composition and ATP will be comprised in another compartment comprising the powdery solid phase, physically separated from the aqueous extracts. More particularly the aqueous extract of watercress is an aqueous extract of watercress aerial parts, and even more particularly an aqueous extract of watercress leaves. Particularly, the extract of Indian cress is an aqueous extract of Indian cress aerial parts, in particular of leaves.

In such a topical composition, the solid phase in powder form is composed of dermatological or cosmetic active agents and/or excipients selected from the group consisting of: amorphous silica, cyclodextrin(beta), stearyl glycyrrhetinate, sodium cocoyl glutamate, lactose, ATP, surfactants, alone or in mixture.

The surfactants can be selected from anionic derivatives and more particularly magnesium lauryl sulphate, lauryl sulfosuccinate and sodium cocoylisethionate, non-ionic derivatives and more particularly lauryl alcohol ethoxylate and the nonylphenols; cationic derivatives and more particularly cetyldimethylbenzyl ammonium bromide and cetyltrimethyl ammonium chloride; amphoteric derivatives and more particularly lauryl betaine and derivatives of imidazoline and their mixtures.

The solid phase can comprise emulsifiers and more particularly whey and egg lecithin powder.

This solid phase can in particular comprise active principles which are relatively unstable in solution and/or difficult to dissolve. Preferentially, therefore, this powdery solid phase comprises the ATP of the compositions according to the invention.

The lipophilic phase is composed of at least one cosmetically or dermatologically acceptable plant or animal or mineral oil, alone or in mixture. The plant oil can be selected from the group consisting of sweet almond oil, avocado oil, coconut oil, wheat germ oil, corn oil, olive oil, palm oil, sesame oil, soybean oil, argan oil, oenothera oil, borage oil, hydrolysed squash seed oil, the essential oils and the plant waxes, as well as their mixtures. The essential oils can be selected from the sweet orange or lavender essential oils, for example.

The mineral oil can be a cosmetic or dermatological oil selected from the paraffin series, or liquid petrolatum, silicone oil; for example dodecane or tetradecane.

The lipophilic phase can also comprise a fatty/oily phase comprising or composed of fatty esters, such as vitamin A fatty esters, in particular tocopheryl acetate.

The lipophilic phase can also comprise animal oils and more particularly beaver oil, turtle oil, mink oil, fish oils and animal waxes.

According to the present invention, this lipid phase can also contain stable lipophilic derivatives and more particularly dyes, sunscreens, antioxidants, preservatives and also active principles.

The aqueous phase can contain stable water-soluble derivatives and more particularly dyes, preservatives, and also water-soluble active principles.

The aqueous phase can comprise the following compounds: 96% ethyl alcohol, pyridoxin hydrochloride, hesperidin methyl chalcone, purified water, niacinamide, hydroalcoholic extract of *Pfaffia* roots, aqueous extract of watercress, aqueous extract of Indian cress, dyes, used alone or in mixture.

The aqueous phase particularly comprises the combination of the aqueous extract of watercress and the aqueous extract of Indian cress as mentioned above.

According to the present invention, the triphasic formulation contains 0.1 to 10 wt % of the solid phase, 1 to 50 wt % of the lipophilic phase and 10 to 90 wt % of the aqueous phase.

Lastly, according to a preferred formulation, the composition preferably contains 1 to 5 wt % of the solid phase, 10 to 25 wt % of the lipophilic phase and 50 to 70 wt % of the aqueous phase.

The invention thus relates in one of its embodiments to a cosmetological and/or dermatological topical composition, characterized in that it comes in the form of three distinct phases, intended to be mixed immediately before use so as to obtain an emulsion and/or a microemulsion, said phases being:
- a solid phase containing ATP in a powdery form,
- an aqueous phase containing an aqueous extract of watercress and an aqueous extract of Indian cress and
- a lipophilic phase.

Such a triphasic composition is particularly suitable for use in the preventive or curative treatment of alopecia.

A combination or a composition according to the invention is particularly suited to be employed in a process for cosmetic treatment of the scalp allowing to obtain a head of hair which provides greater coverage comprising the application of the combination or the composition to the scalp, particularly between 1 and 3 times per week.

Preferentially the application of a combination or a composition according to the invention is not followed by rinsing.

A triphasic composition according to the invention as described above is particularly suited to be employed in a process for cosmetic treatment of the scalp allowing to obtain a head of hair which provides greater coverage comprising the application of the composition to the scalp, particularly between 1 and 3 times per week.

Preferentially the application of a combination or a composition according to the invention is not followed by rinsing.

The compositions according to the invention can also be administered via the oral route. In this case, the suitable unit dosage forms comprise the forms suitable for an oral route, such as tablets, capsules, powders, granules and oral solutions or suspensions.

These compositions generally contain, in addition to the compounds of the combination according to the present invention, a physiologically acceptable medium, in general water- or solvent-based, for example alcohols, ethers or glycols. They can also contain surfactants, sequestrants, preservatives, stabilizers, emulsifiers, thickeners, gelling agents, wetting agents, emollients, trace elements, essential oils, fragrances, dyes, hydrating agents or spring water, etc.

Advantageously, the compositions according to the present invention will comprise 0.01 to 1 wt %, preferably 0.01 to 0.5 wt %, in a preferred manner 0.02 to 0.1 wt %, in a more preferred manner 0.02 to 0.05 wt % of extract of watercress, particularly of aqueous extract of watercress, relative to the total weight of the composition. In a preferred manner, the composition will comprise about 0.02 wt % of extract of watercress, particularly of aqueous extract of watercress, relative to the total weight of the composition.

Advantageously, the compositions according to the present invention will comprise 0.01 to 1 wt %, preferably 0.01 to 0.5 wt %, in a preferred manner 0.02 to 0.1 wt %, in a more preferred manner 0.02 to 0.05 wt % of extract of Indian cress, particularly of aqueous extract of Indian cress, relative to the total weight of the composition. In a preferred manner, the composition will comprise about 0.02 wt % of extract of Indian cress, particularly of aqueous extract of Indian cress relative to the total weight of the composition.

More particularly the aqueous extract of watercress is an aqueous extract of watercress aerial parts, and even more particularly an aqueous extract of watercress leaves. Particularly, the extract of Indian cress is an aqueous extract of Indian cress aerial parts, in particular of leaves.

In a preferred manner, the compositions according to the invention will comprise the same percent content of extract of watercress and of Indian cress, particularly of aqueous extract of watercress and of Indian cress, relative to the total weight of the composition.

Advantageously, the compositions according to the present invention will comprise 0.1 to 1 wt %, preferably 0.1 to 0.5 wt %, in a preferred manner 0.2 to 0.5 wt %, in a more preferred manner 0.25 to 0.4 wt % of ATP relative to the total weight of the composition. In a preferred manner, the composition will comprise about 0.3 wt % of ATP relative to the total weight of the composition.

In a particular manner, when the amounts of extract of watercress, extract of Indian cress and ATP in the ternary combination according to the invention are expressed in parts, this combination comprises between 0.5 and 2 parts extract of Indian cress, between 0.5 and 2 parts extract of watercress and between 5 and 20 parts ATP. In a preferred manner, the combination according to the invention comprises, in parts, 1 part extract of Indian cress, 1 part extract of watercress and 15 parts ATP. More particularly they are aqueous extracts of watercress and of Indian cress. More particularly the aqueous extract of watercress is an aqueous extract of watercress aerial parts, and even more particularly an aqueous extract of watercress leaves. Particularly, the extract of Indian cress is an aqueous extract of Indian cress aerial parts, in particular of leaves.

The light texture of said composition further allows optimal penetration without making the hair greasy. From the first applications, the hair regains strength and vitality.

The composition according to the invention allows to stop hair loss and to extend the hair cycle. Existing hair is preserved in quantity and in quality.

In a particular embodiment, the cosmetic or dermatological compositions according to the invention comprise at least one other anti-alopecia active principle.

Another object of the present invention relates to the cosmetic use of the combination according to the present invention or of this cosmetic composition according to the invention to promote hair growth and/or to obtain a head of hair which provides greater coverage. The cosmetic use of the combination according to the present invention or the cosmetic intended to regulate the hair cycle and to promote follicular regeneration.

The present invention also relates to a process for cosmetic care of the hair intended to improve the aesthetic quality of the hair by promoting hair growth and/or to obtain a head of hair which provides greater coverage, characterized in that it consists in applying to the hair and the scalp an effective amount of a combination according to the invention or of a cosmetic composition according to the invention, in leaving same in contact with the hair, and optionally in rinsing the hair.

Such compositions can be manufactured according to processes well-known to the person skilled in the art.

The examples which follow are intended to illustrate certain particular embodiments of the invention and represent in particular certain compositions that can be used for implementing the invention. The excipients mentioned in the composition examples are given only by way of illustration, and it is within the scope of the person skilled in the art to substitute them with others.

EXAMPLE 1: PHARMACOLOGICAL TEST OF AN AQUEOUS EXTRACT OF WATERCRESS AND OF INDIAN CRESS, OPTIONALLY COMBINED WITH ATP

The goal of this study is to evaluate the effects of the combination of an aqueous extract of watercress and of an aqueous extract of Indian cress, combined with ATP on the release of 2 anagen phase markers, hepatocyte growth factor (HGF) and keratinocyte growth factor (KGF), released by dermal papilla cells. These two growth factors have a stimulatory activity on hair growth by activating specific signalling pathways.

The studies were carried out on dermal papilla cells derived from human hair follicles from three different donors. The cells are seeded in 24-well plates and cultured for 24 h with the necessary supplements. The cells are then treated for 24 h with the products, i.e., either with ATP (30 µM), with Cressatine®, i.e., an aqueous extract of watercress and an aqueous extract of Indian cress (140 µg/ml), or with the combination ATP-Cressatine® at the same concentrations as before. The supernatants were collected for subsequent analysis of markers HGF and KGF. HGF is measured using set HCCBP1MAG-58K from EMD Millipore and KGF is measured by using set KGF/FGF-7 DuoSet ELISA DY251 from R&D Systems.

The results are summarized in the following tables.

HGF Release:

30 µM ATP alone does not significantly modulate the production of HGF (Tables 1). The 140 µg/ml aqueous extracts of watercress and of Indian cress induce a significant increase in the production of HGF (p<0.01 versus control); this increase reaches 66%. When they are combined, 30 µM ATP and 140 µg/ml Cressatine® induce a significant and very marked increase in HGF release; this increase reaches 133%. The induction obtained with this combination is significantly higher than that obtained with Cressatine® alone, thus showing the synergistic effect of these compounds.

TABLE 1

HGF release by dermal papilla cells derived from human hair follicles. The results are expressed as average values of the 3 donors ± SEM (SEM = standard error of the mean).

|  | HGF (pg/ml) | SEM | Comparison, Dunnett's test Vs control | Vs Cressatine ® |
| --- | --- | --- | --- | --- |
| Control | 80 | 17 | — | — |
| ATP | 92 | 21 | P = NS | — |
| Cressatine ® | 120 | 25 | P < 0.01 | — |
| ATP + Cressatine ® | 167 | 37 | P < 0.01 | P < 0.01 |

Cressatine ®: aqueous extract of watercress and of Indian cress.

KGF Release:

30 µM ATP alone is capable of significantly stimulating the production of KGF (Table 2) and induces 50% higher secretion. The 140 µg/ml aqueous extract of watercress and of Indian cress alone does not induce a significant increase in this release. On the other hand, the combination of these compounds at the same concentrations induces a substantial and significant release of KGF; this increased production is higher than that obtained with ATP alone, thus showing the synergistic effect of these compounds.

TABLE 2

KGF release by dermal papilla cells derived from human hair follicles. The results are expressed as average values of the 3 donors ± SEM (SEM = standard error of the mean).

|  | KGF (pg/ml) | SEM | Comparison, Dunnett's test Vs control | Vs Cressatine ® |
| --- | --- | --- | --- | --- |
| Control | 26 | 4 | — | — |
| ATP | 37 | 5 | P < 0.01 | — |
| Cressatine ® | 32 | 9 | P = NS | — |
| ATP + Cressatine ® | 48 | 11 | P < 0.01 | P < 0.01 |

Cressatine ®: aqueous extract of watercress and of Indian cress.

In conclusion, ATP alone stimulates the production of KGF, the aqueous extract of watercress and of Indian cress allows to increase HGF release, and the combination ATP and Cressatine® synergistically stimulates the production of HGF and of KGF. Thus, the synergistic effect of these 2 compounds allows to stimulate hair growth, to strengthen and to extend the hair lifecycle, to delay and to slow hair loss and thus to obtain a head of hair which provides greater coverage.

EXAMPLE 2: EXAMPLE OF A TRIPHASIC COMPOSITION ACCORDING TO THE INVENTION

| Alcohol | 10 to 40% |
| --- | --- |
| Powder (lactose) | 1 to 2% |
| Oily emollients | 10 to 20% |
| Aqueous emollients | 1 to 5% |
| Watercress (in the aqueous phase) | 0.01 to 0.5% |
| Indian cress (in the aqueous phase) | 0.01 to 0.5% |
| ATP (in the powder) | 0.1 to 0.5% |
| Dye | <0.1% |
| Water | qs |

The percentages expressed correspond to weight % relative to the total composition.

The three phases are mixed immediately before use, the whole is shaken to ensure solubilization of the powdery ingredients in the aqueous phase and emulsification of the aqueous and oily phases.

The composition obtained is applied to the scalp and is not rinsed.

The invention claimed is:

1. A combination comprising an aqueous extract of watercress aerial parts, an aqueous extract of Indian cress aerial parts and 0.1 to 0.5% wt. ATP relative to the total weight of the composition.

2. The combination according to claim 1, for use in the treatment of alopecia.

3. The combination for use according to claim 2 wherein the alopecia is selected from the group consisting of androgenic alopecia, postmenopausal alopecia, acute alopecia and alopecia areata.

4. A method of promoting hair growth which comprises applying to the hair and the scalp an effective amount of the combination according to claim 1.

5. A cosmetic or dermatological composition comprising as an anti-alopecia active principle the combination according to claim 1, further comprising at least one cosmetically or dermatologically acceptable excipient.

6. The composition according to claim 5, characterized in that it comprises 0.01 to 0.5 wt % of an aqueous extract of watercress relative to the total weight of the composition.

7. The composition according to claim 5, characterized in that it comprises 0.01 to 0.5 wt % of an aqueous extract of Indian cress relative to the total weight of the composition.

8. The composition according to claim 5, characterized in that it further comprises another anti-alopecia active principle.

9. The composition according to claim 5, characterized in that it comes in a form suitable for topical application.

10. A method of promoting hair growth and/or obtaining a head of hair which provides greater coverage which comprises applying to the hair and the scalp an effective amount of the composition according to claim 5.

11. The composition according to claim 5, for use in the treatment of alopecia.

12. A process for cosmetic care of hair to improve the aesthetic quality of the hair by promoting hair growth and/or to obtain a head of hair which provides greater coverage, which comprises applying to the hair and the scalp an effective amount of the combination according to claim 1 leaving said combination in contact with the hair, and optionally in rinsing the hair.

13. A method of treating alopecia which comprises applying to the hair and the scalp an effective amount of the combination according to claim 1.

14. A method of treating alopecia which comprises applying to the hair and the scalp an effective amount of the composition according to claim 5.

* * * * *